United States Patent [19]
Bolton et al.

[11] Patent Number: 4,824,209
[45] Date of Patent: Apr. 25, 1989

[54] LIGHT SOURCE ASSEMBLY

[75] Inventors: Joseph A. Bolton, Queensbury; Raymond W. Beck, Fort Ann; Robert B. Ramey, Whitehall, all of N.Y.

[73] Assignee: Albany International Corporation, Menands, N.Y.

[21] Appl. No.: 176,108

[22] Filed: Mar. 30, 1988

[51] Int. Cl.[4] .............................................. G02B 7/00
[52] U.S. Cl. .................................... 350/319; 350/321; 362/31; 40/588
[58] Field of Search .................. 350/319, 321; 362/26, 362/27, 28, 29, 30, 31; 250/559, 560, 563; 356/239, 241; 40/558, 553, 546

[56] References Cited
U.S. PATENT DOCUMENTS 3,241,256  3/1966  Viret et al. ............................. 362/30
3,684,882  8/1972  Mininno et al. ....................... 40/546
4,284,356  8/1981  Heilman ............................... 250/559
4,319,840  3/1982  Kondo et al. ......................... 356/239
4,386,476  6/1983  Schulman ............................. 40/546

Primary Examiner—John K. Corbin
Assistant Examiner—Loha Ben
Attorney, Agent, or Firm—Kane, Dalsimer, Sullivan, Kurucz, Levy, Eisele and Richard

[57] ABSTRACT

A light assembly for generating a narrow light beam of relatively uniform intensity for use in association with a light sensor for sensing variations in light intensity; the assembly includes a plurality of standard size aperture light bulbs positioned in a staggered arrangement in a housing with light extender members comprising alternating sheets of light transmissive material joined to form a common surface to generate the light beam.

15 Claims, 4 Drawing Sheets

FIG. I

LIGHT SOURCE ASSEMBLY

FIELD OF THE DISCLOSURE

The present invention is directed toward providing a light source, particularly one which is of high intensity and uniformity for use in the analysis of product.

BACKGROUND OF THE INVENTION

In the nonwoven and paper industries, webs of material are produced at very high rates of speed. An important consideration in such manufacture is the monitoring of the formation of the web. The quality of the non-woven paper material is always important to the quality of the end product produced.

Formation to most web manufacturers is the degree of uniformity achieved in the distribution of the fiber mass within the web. A well formed web is one where the fibers are randomly dispersed throughout. Well formed webs are usually stronger and have better appearance, which is important to the end user.

Good formation is especially important to non-woven and paper manufacturers. Poor formation not only adversely effects a web or sheet appearance, but also effects its printability and other qualities.

The traditional methods of classifying the formation of non-woven webs and paper sheets has been with human inspection and off-line formation sensors. The describing of a given web or sheet as being good, not bad, flocky, streaky, etc., is very relative and subjective. Studies in general have shown very poor agreement between visual and off-line formation sensors.

The problems with off-line formation sensors is the time between sample and results and also obtaining good profile measurements. At the speeds most modern non-woven and paper manufacturers run thousands of yards of material can be off quality before the results from the lab are obtained.

Studies made of variations in formations of paper webs have shown more variations across the web versus downweb. Therefore, the need for continuous updating of formation profile measurements is important.

To help eliminate the problems with human inspection of webs and the use of off-line sensors, manufacturers are starting to use single point formation sensors on-line. Some are fixed on the machine while others are slowly traversed across the web. Most of these sensors use the principle of comparing the light intensity of a small area, 1 mm or less, with a larger area, say of 30 mm diameter or larger. A formation index is based upon the intensity variation in the small area as compared to the average light intensity of the larger area.

The problem to date with these on-line single point formation sensors has been with the repeatability of the results with changing machine speeds and products. Another problem has been in getting rapid formation profile measurements across the web in less time than, for example, a minute of operation.

A further improvement to these on-line single point formation sensors is the use of a linear array CCD (charged coupled device) camera which looks at the variations in light intensities across the entire moving web without traversing. This technology was an outgrowth of using linear array CCD cameras to inspect for defects in moving webs. Defects like holes or dark spots would cause the light intensity at a given area in the web to exceed from its normal range and cross a given light or dark threshold, thus signaling a defect has been detected. One such system is being marketed by Albany International, assignee of the present application, under the name WEBSPEC TM.

In such a system an automatic, high-speed visual web inspection system is provided. A full web width high-intensity light source is used to shine through the moving web. A linear CCD camera with a zoom lens is focused on the streak of light passing through the web. The camera contains a given number of solid-state, photo-sensitive diodes used to detect the variation in light intensities across the web. An analog electrical signal, proportional to the light intensity detected by the respective photo-sensitive diodes, is sent to the computer system. Normally, all the photo-sensitive devices in the camera are used to scan the web once. Therefore, if the camera contains 2,048 devices, the number of picture elements or "pixels" per scan would equal 2,048.

The analog signals from the devices are converted to digital for binary and digital image analysis by the computer system. The analog signals from the camera are normalized, compared to threshold settings and processed with a 68000 microprocessor. An information summary on the type, size and location of the defects detected can be either stored on disk or a hard copy made using a printer and a flagger is activated to place a flag adjacent a defect in the downweb direction.

While such a defect identifier has proven eminently satisfactory for defect detection, another aspect of web analysis involves, as aforenoted, that of the formation of the web. The formation quality of paper is defined as the degree of uniformity achieved in the distribution of fiber mass. A well formed sheet is one where the fibers are very randomly dispersed throughout the entire sheet. Good formation is essential during papermaking because it strongly affects the appearance and printability of the sheet. In general, poor formation adversely effects other sheet qualities. Well formed paper is stronger, more uniform, easier to dry and allows the paper to run better.

Describing a given paper sample or sheet as good, not bad, poor, floccy, streaky, etc., indicates that formation is very subjective. Studies by the Institute of Paper Chemistry (Paper Trade Journal, May 30, 1984) concluded that reproducibility of visual formation gradings between different observers was relatively poor. A better formation grading was obtained between a Thwing-Albert formation tester and the average of the visual results.

Because of these difficulties and the importance of good formation to the papermaker, an effort has been made to develop a so-called "standard formation tester or sensor" which could be used either on or off line. Some of the testers developed over the years include the QNSM, NUI, MKS, Thwing-Albert, Microscanner TM, Toyoseiki, Lippke and more recently, the Opti Pak TM. All have been used by papermakers to help quantify the formation they were obtaining and to make quality improvements.

However, there was a need for a full width which can run from 12-35 feet wide, real time formation sensor for paper machine applications which has not heretofore been achieved. This is especially true, since on most paper machines, variation in formation across the web (C.D. or X.D.) is much greater than in the downweb direction.

To meet this need there was developed a device for web formation analysis which is set forth in U.S. patent application Ser. No. 159,830, filed Feb. 24, 1988, entitled "Method And Apparatus For Analyzing A Web Of Material", which is commonly assigned to Albany International Corporation, the assignee of the present application, the disclosure of which is incorporated herein by reference.

The system which is entitled the FORMSPEC TM system by Albany International involves the use of a linear array CCD camera to measure the variation of transmitted light through a moving web. The light intensities across the entire web are converted into analog electrical signals and, in turn, digital signals. The linear array CCD camera is effective in determining differences in the formation of the paper web. A formation index is generated from the information generated by electronic scanning. The system measures the light intensity across the web of material which can run from 12-18 feet in width.

In such web analysis, it is accordingly important that the light source not only be of high intensity, but also uniform. Variation of the light intensity can be erroneously construed as variations in the web formation leading to improper results. While the use of custom-made lighting is possible, such as twelve foot lengths of high intensity aperture bulbs, such lighting is expensive and suffers from a fall off in intensity at its ends. It is therefor desirable that a light assembly be provided which is effective in operation but relatively inexpensive in cost of manufacture.

SUMMARY OF THE INVENTION

It is therefore a principal object of the invention to provide for a high intensity light assembly which provides a uniform output of light.

It is a further object of the invention to provide for such a light assembly which is relatively inexpensive in cost.

It is yet a further object to provide for a light assembly which utilizes certain standard parts readily available in the industry as a light source.

The present invention provides for a high intensity light having uniform luminescence throughout its length. The purpose of the light is to shine through, for example, a web of material for formation analysis. The assembly provides concentrated light in a narrow band across the entire width of a web which is being analyzed. The light is uniform and is generated by a series of aperture bulbs positioned in a housing having a longitudinal slot therein. The aperture bulbs, which are of a standard size either 4 feet or 8 feet long, are offset from the slot in a staggered arrangement. Coupling the light aperture to the slot is a series of light transmitting members such as Plexiglass TM. Since the light must be uniform all across and even the smaller bulbs fall off in intensity at their ends, the entire bulb length cannot be used. Accordingly, the bulbs need to overlap to a certain degree. To allow for this, the Plexiglass TM members comprises a straight portion which extends to the slot and a bent portion which extends to the bulb which is offset from the slot. This allows for the staggering of the bulbs in an overlapping manner on opposite sides of the slot. Thus a uniform light intensity is generated in the slot via the Plexiglass TM members with standard size bulbs which reduce the costs involved.

BRIEF DESCRIPTION OF THE DRAWINGS

Thus by the present invention, its objects and advantages will be realized, the description of which should be taken in conjunction with the drawings, wherein.

DETAILED DESCRIPTION OF THE PREFERRED EMBODIMENT

Turning now more particularly to the drawings, there is shown a light source assembly 10 (in FIG. 1) broken into sections because of its length. The assembly 10 is in the nature of an elongated rectangular structure which is intended to have a web of material for analysis pass width-wise over the slot 12 which is formed between support members 14 and 16 and wear strips 14a and 16a, respectively. The size and material used for the wear strip may vary with application or as so desired.

Figure 1:
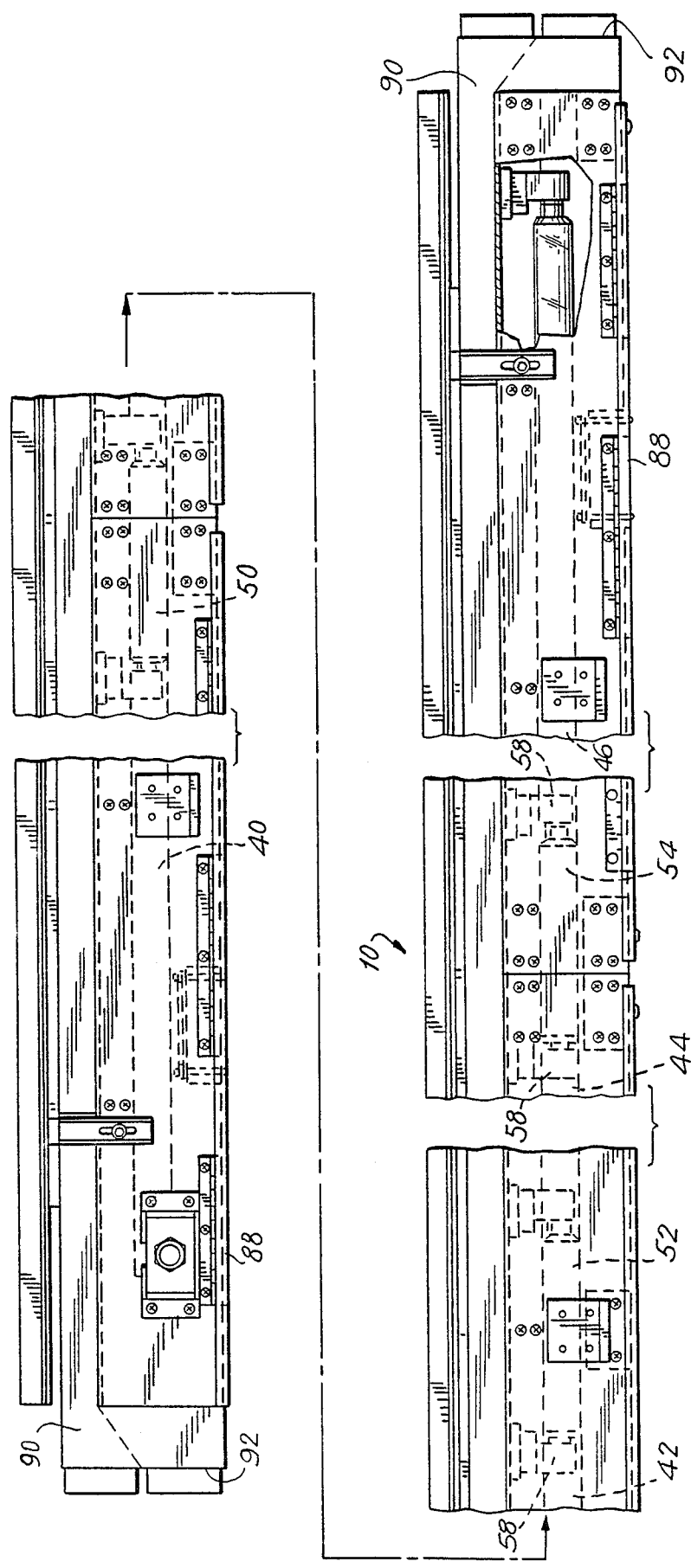
FIG. 1 is a side partially sectional view of the light assembly incorporating the teachings of the present invention.

A housing 18 is provided and comprises side walls 22 and 24 which may be braced to top and bottom U-shaped panels 26 and 28 via appropriate fasteners 30. Support members 14 and 16 can be similarly fashioned to the side walls. The top panel 26 includes angled openings 32 and 34 to allow for a series of light extensions 36 and 38 to pass. The light extensions 36 and 38, which will be more fully discussed, comprise a series of transparent members, preferably made of plastic, but which also may be of glass, extending in an alternating fashion, along the length of the assembly. In this regard, the light extensions allow for the overlapping of the light generated by light bulbs so as to advantageously avoid the loss of intensity at bulb ends and, in addition, allow for use of standard size (i.e., 4' or 8') bulbs. As can be seen in FIG. 1, a series of bulbs 40, 42, 44 and 46 are shown. With, for example, a 4 foot light bulb, only approximately 37.5" of its length can be used for light generation due to end fall off. Accordingly, using such standard bulbs, an overlapping is provided, for example, as between bulbs 40 and 42, they overlap at area 50; 42 and 44 at area 52; 44 and 46 at area 54. At the far ends of bulbs 40 and 46, a portion of these would not be used for light generation and accordingly, the light extenders used in association therewith would begin at a certain distance inwardly from the ends.

The bulbs used are standard aperture type bulbs such as those produced by Sylvania VHO F 48 T12/CW/PB/130 providing 115 watts. Aperture bulbs includes a coated, frosted inner surface with a small portion 56 thereof or aperture strip running in a straight line along its longitudinal length so as to concentrate the light output at that point.

The light bulb assembly includes standard electrical mounting prong sockets 58, typically used with florescent lighting at both ends of the bulbs which may be affixed to and supported by the housing, particularly the upper panel. Note, the sockets 58 are so oriented such that the aperture 56 of the bulb upon the latter being inserted and turned into position, align the aperture with the bottom portion 60 of the respective light extensions 38. If not aligned, then the bulb has been inserted upside down or end for end so that the aperture would be off by 180°, easily indicating improper alignment and that it must be corrected.

Once the bulb is in place, respective clamping members 62 are used. Two arm extensions 64 serve to engage either sides of the bottom portion 60 which is aligned with the aperture portion 56. Upon tightening the adjustment screws 66, the bulb is fixed in position with the bottom portion 60 of the light extenders and prevented from becoming misaligned.

It should be noted at this point that while the bulbs are electrically connected in a typical fashion, it has been found beneficial to use a high frequency ballast rather than the typical 60 cycle ballast. The reason for this is that at the lower cycle, fluctuation in light intensity may occur. This becomes important since in certain applications the speed of the camera scan which, for example, may be on the order of 5,000 scans per second. Such a scanning rate could be affected by a light fluctuating. Accordingly, high frequency ballast, such as that manufactured by The Bodine Company, Collerville, Tenn., sold under the name Tran-Bal ™, which operates at 24 Khz may be utilized to avoid this problem.

Returning now to the housing, included on the opposite side of panel 28 are respective air feed tubes 68 on which are mounted via mounting bolts, L-shaped angle supports 69 between which the upper portions 70 of the light extension members are positioned. Note, these supports may be fabricated out of metal or plastic, as may many of the parts suitable for purpose.

The upper portion 70 is intended to run in consecutive segments of alternating positioned lower portions so as to make up one long light extension member of, for example, 12′ when such a width is desired.

What is important is that the joints between adjacent members is such so as to minimize light loss or differentiation in that joint. Initially, the material utilized for the light extension member may be any luminous transmitting substance such as glass or plastic, with sufficient transparency suitable for purpose. What has become particularly suitable is Plexiglass ™ Clear G, which is a cast acrylic sheet having optical properties per ASTM D-1003, 1% or less haze, and 91 or better total luminous transmittance.

The light extension member is rectangular and approximately ⅜″ thick and includes a flat upper surface 72, upper side surface 74 located on opposite ends along upper portion 70 between surface 72 and bend 76, and a bottom surface 78 which is to be positioned adjacent the apertures in the bulbs.

All surfaces should be ground smooth and polished. The angle of the bottom portion 60 to that of the top portion 74 is approximately 15° but can be larger or smaller but not so great to cause the light not to bend properly.

Figure 2:
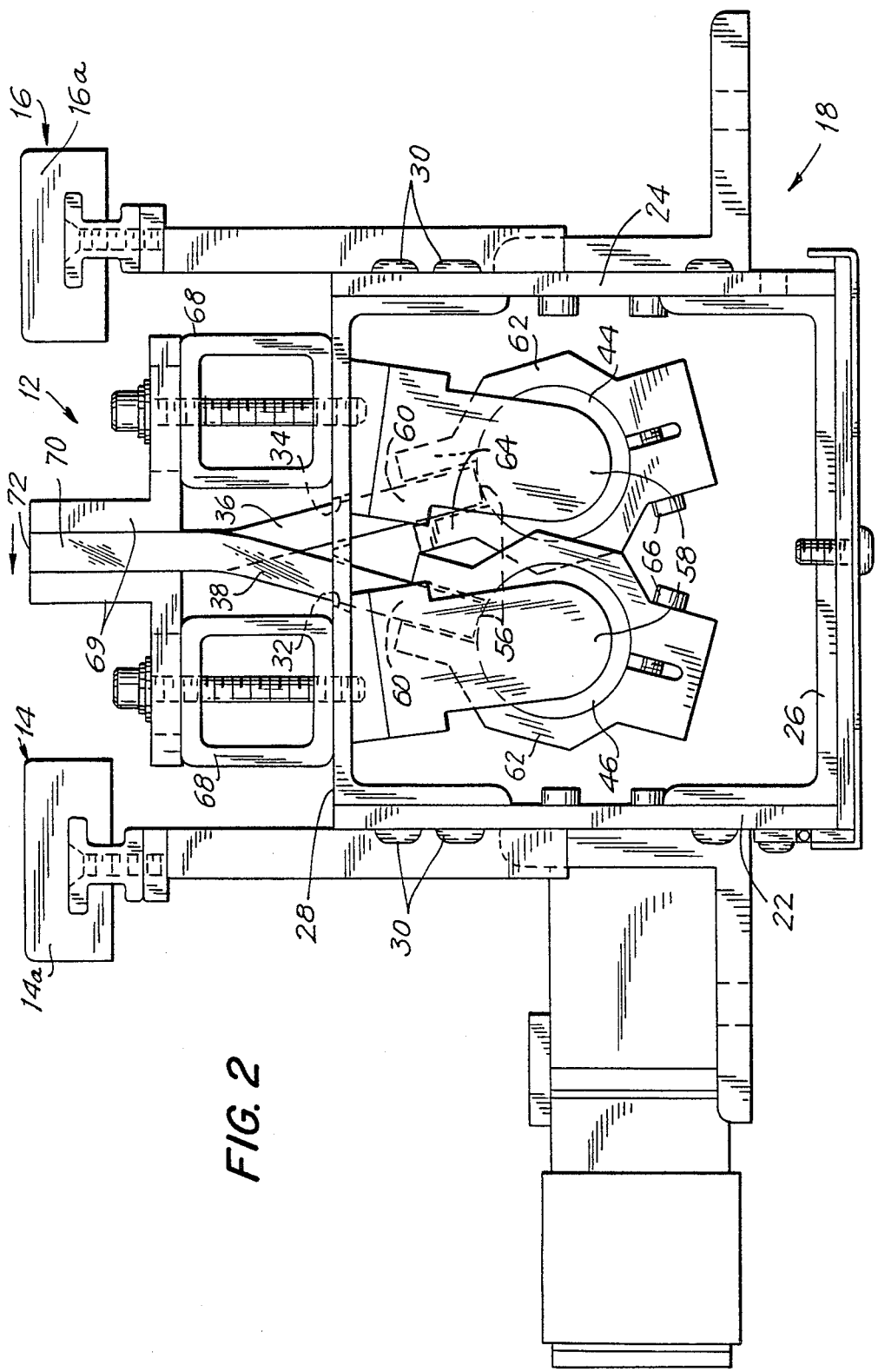
FIG. 2 is a cross-sectional view of the light assembly incorporating the teachings of the present invention.
Figure 3:
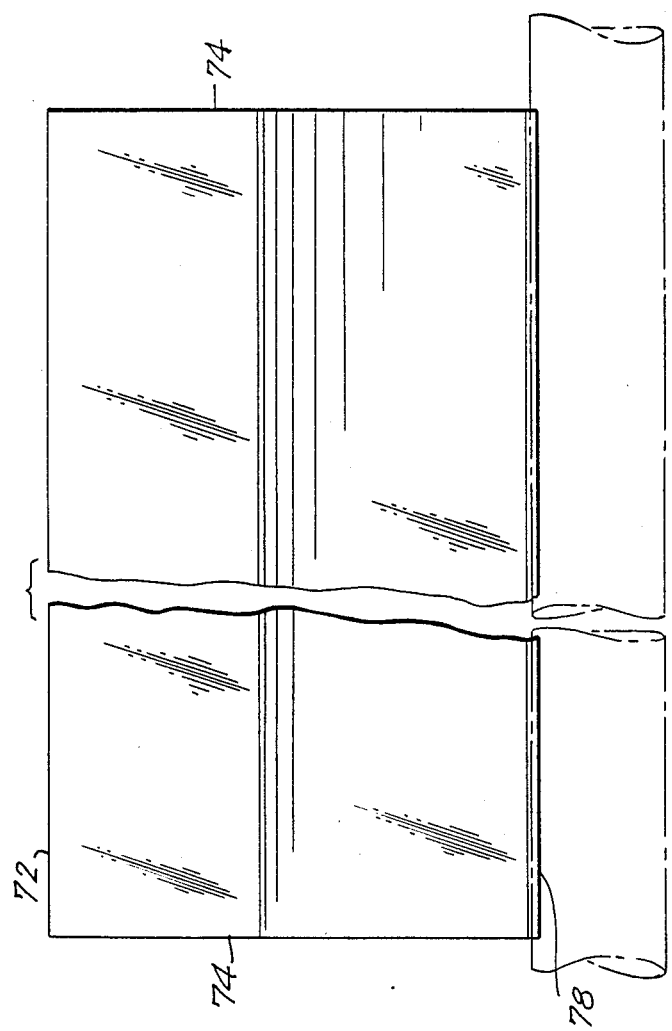
FIG. 3 is a side view of the light extension member for the light source incorporating the teachings of the present invention.

The respective sections of light extension members are then fastened together in an alternating fashion, that being as looking into FIG. 2, bottom portion to the left, next to the right, next to the left and so on. For a 12 foot width, at least 12 feet of attached members would be utilized, each of which would lie adjacent the apertures of the respective bulbs along approximately 75% of the bulb length.

The upper side surfaces 74 of the adjacent lengths of light extenders are joined together by way of a clear glue or optical cement to lessen the loss of light via the joint. The light extension member is positioned in the assembly with the upper portion 70 being fixedly maintained to between the angle supports 69.

Figure 5:
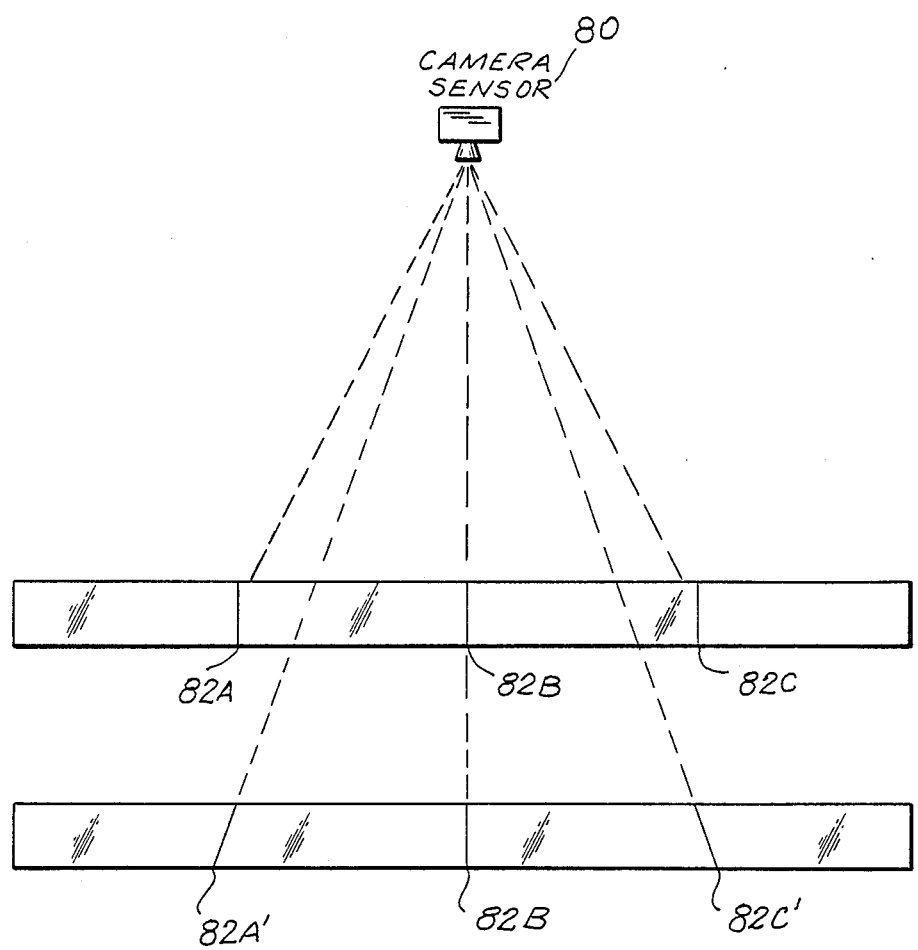
FIG. 5 is a schematic view of a portion of the light assembly, particularly the light extension members in association with a sensor, incorporating the teachings of the present invention.

In operation, the light from the bulbs is focused upward and exits at surface 72 and ultimately through a web of material. The light passing through the web is scanned by a sensor such as a CCD camera along the light assembly. A schematic of this is shown in FIG. 5. A sensor 80 is shown positioned above the light extending members. Three joints at 82A, 82B and 82C are illustrated. As the sensor scans across the web, it remains in one position. As such, if the surfaces 74 between the adjacent members are cut straight as shown at joints 82A and 82C, the effect of the joint on light passing through and as seen by the sensor will be greater than the adjacent area. Rather than a sensor seeing a single line as at 82B, it sees a wider line at 82A and 82C because the joints there are at an angle to the line of scan. If however the joints at 82A′ and 82C′ are cut at an angle to the line of scan as shown, the sensor would see less of a joint and therefor less variation of light at the joint providing a better result.

Figure 4:
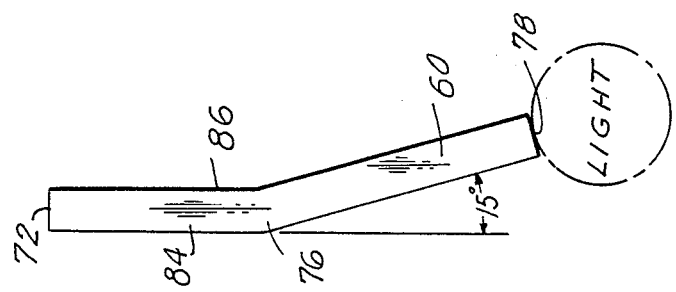
FIG. 4 is a cross-sectional view of the light extension member for the light source incorporating the teachings of the present invention.

In addition, returning to FIG. 4, as an alternative configuration to that shown, the use of mirrored surfaces on planar surfaces 84 and 86 may serve to increase the light output from surface 72 and inhibit the diffusion of light therefrom.

Since the light assembly generates heat during its operation, a cooling system is provided and can comprises exhaust fans 88 which would take in air by way of intakes 90. Alternatively, forced air could be used which flows through intakes 90 and exits via outlets 92. Either system, or any other which keeps the assembly cool, may be utilized.

Thus by the present invention, its objects and advantages are realized and although a preferred embodiment has been disclosed and described in detail herein, its scope should not be limited thereby, rather its scope should be determined by that of the appended claims.

What is claimed is:

1. A light assembly for generating a narrow beam of light of relatively uniform intensity for use in association with a light sensor for sensing variations in light intensity, said assembly comprising:
   a source of light which includes a plurality of elongated bulbs having longitudinal axes;
   light extending means comprising at least two sheets of light transmissive material, said means functions to channel light from the light source into a narrow, relatively uniform, longitudinal path defining a slot; and
   the axes of at least two of said bulbs being non axially aligned and said two bulbs extending in a manner that an end portion of one is in juxtaposition with respect to that of the other so that light is uniformly transmitted through the light extending means in an alternating manner.

2. The invention in accordance with claim 1, wherein said light extending means includes a plurality of sheets of light transmission material which are joined together at a joint to form a uniform surface along a first portion of each of said sheets adjacent and axially aligned with said slot, said sheets comprise second portions divergent from said first portions in alternating fashion such that end surfaces of said second portions being positioned adjacent respective bulbs.

3. The invention in accordance with claim 2, wherein said bulbs have apertures and said apertures being axially aligned with said end surfaces respectively.

4. The invention in accordance with claim 3, wherein a portion of the sheets form a flat surface defining the slot with said flat surface being ground smooth and polished.

5. The invention in accordance with claim 4, wherein said first portions are ground and polished at the joint and bound by optical cement.

6. The invention in accordance with claim 5, which includes respective clamping means for clamping said second portions of said light extending means into axial positions with said apertures.

7. The invention in accordance with claim 6, wherein a web of material passes over said slot, said assembly further includes wear strips positioned adjacent said slot to support the web as it passes over the slot.

8. The invention in accordance with claim 7, wherein sensor means comprises a camera positioned above said slot capable of scanning thereacross, said joints in said light extending means being formed at an angle corresponding to the angle of the camera scan at the point of the joint.

9. The invention in accordance with claim 8, which includes a housing supporting said light source and light extending means and means for cooling same.

10. The invention in accordance with claim 9, wherein said light extending means comprises sheets of clear acrylic material.

11. The invention in accordance with claim 9, wherein said light extending means comprises sheets of glass.

12. The invention in accordance with claim 2, wherein sensor means comprises a camera positioned above said slot capable of scanning thereacross, said joint in said light extending means being formed at an angle corresponding to the angle of the camera scan at the point of the joint.

13. The invention in accordance with claim 1, which includes a housing supporting said light source and light extending means and means for cooling same.

14. The invention in accordance with claim 1, wherein said light extending means comprises sheets of clear acrylic material.

15. The invention in accordance with claim 1, wherein said light extending means comprises sheets of glass.

* * * * *